(12) United States Patent
Adams et al.

(10) Patent No.: US 11,160,627 B2
(45) Date of Patent: Nov. 2, 2021

(54) CABLE DRIVEN MOTION SYSTEMS FOR ROBOTIC SURGICAL TOOLS

(71) Applicant: Ethicon LLC, Guaynabo, PR (US)

(72) Inventors: Eric Adams, Pittsboro, NC (US); John Evans, Appleton, WI (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/034,909

(22) Filed: Sep. 28, 2020

(65) Prior Publication Data

US 2021/0007818 A1  Jan. 14, 2021

Related U.S. Application Data

(63) Continuation of application No. 15/794,555, filed on Oct. 26, 2017, now Pat. No. 10,786,320.

(51) Int. Cl.

| | |
|---|---|
| *A61B 34/00* | (2016.01) |
| *A61B 34/37* | (2016.01) |
| *A61B 17/29* | (2006.01) |
| *A61B 34/30* | (2016.01) |
| *A61B 17/00* | (2006.01) |
| *B25J 9/10* | (2006.01) |
| *F16H 19/08* | (2006.01) |
| *F16H 1/16* | (2006.01) |

(52) U.S. Cl.
CPC ........ *A61B 34/71* (2016.02); *A61B 17/00234* (2013.01); *A61B 17/29* (2013.01); *A61B 34/30* (2016.02); *A61B 34/37* (2016.02); *B25J 9/1045* (2013.01); *F16H 19/08* (2013.01); *A61B 2017/00477* (2013.01); *A61B 2034/302* (2016.02); *A61B 2034/305* (2016.02); *A61B 2034/715* (2016.02); *F16H 1/16* (2013.01); *F16H 2019/085* (2013.01)

(58) Field of Classification Search
CPC .... B25J 9/1045; F16H 19/08; F16H 2019/085
See application file for complete search history.

(56) References Cited

U.S. PATENT DOCUMENTS

| | | |
|---|---|---|
| 8,831,782 B2 | 9/2014 | Itkowitz |
| 2008/0300462 A1 | 12/2008 | Intoccia |
| 2010/0082041 A1 | 4/2010 | Prisco |

(Continued)

FOREIGN PATENT DOCUMENTS

| | | |
|---|---|---|
| EP | 3066998 B1 | 3/2018 |
| WO | 2011002592 A1 | 1/2011 |

(Continued)

*Primary Examiner* — Vicky A Johnson

(74) *Attorney, Agent, or Firm* — Vorys, Sater, Seymour and Pease LLP

(57) ABSTRACT

A surgical tool includes a drive housing having an input shaft arranged therein for rotation, a shaft extending from the drive housing and having an end effector arranged at a distal end thereof, and a drive cable extending within the shaft and operatively coupled to the end effector. A cable band is coupled to the input shaft and operatively couples the input shaft to the drive cable, and an idler pulley is rotatably mounted within the drive housing, the cable band being routed at least partially around the idler pulley. Rotation of the input shaft moves the cable band and thereby controls longitudinal movement of the drive cable to articulate the end effector.

20 Claims, 10 Drawing Sheets

(56) References Cited

U.S. PATENT DOCUMENTS

2010/0331820 A1* 12/2010 Prisco .................... A61B 34/30
                                                            604/528
2015/0313676 A1    11/2015 Deodhar
2015/0342585 A1* 12/2015 Steege ............... A61B 17/3201
                                                              606/1
2016/0287252 A1* 10/2016 Parihar ............... A61B 17/105
2018/0206930 A1*  7/2018 Suzuki .................. A61B 90/03
2019/0125466 A1*  5/2019 Adams ............. A61B 17/00234
2019/0125467 A1*  5/2019 Evans ................... A61B 34/71
2019/0125468 A1*  5/2019 Adams .................. A61B 34/35

FOREIGN PATENT DOCUMENTS

| WO | 2014151621 A1 | 9/2014 |
| WO | 2014151952 A1 | 9/2014 |
| WO | 2016064616 A1 | 4/2016 |

* cited by examiner

CABLE DRIVEN MOTION SYSTEMS FOR ROBOTIC SURGICAL TOOLS

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint.

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint.

A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations. A number of mechanical and manufacturing hurdles must be overcome through component design and assembly to enable consistent and predictable performance of the end effector and its associated cable driven motion system.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to improved cable driven motion systems that mitigate drive cable derailment risks and provide a constant torque resistance to prevent drive cables from slackening.

Embodiments discussed herein describe surgical tools that include a drive housing having an input shaft arranged therein for rotation, an elongate shaft that extends from the drive housing, and an end effector operatively coupled to a distal end of the elongate shaft. A cable band is coupled to the input shaft and operatively couples the input shaft to a drive cable that extends to the end effector. Rotation of the input drive correspondingly moves the cable band and thereby controls longitudinal movement of the drive cable to articulate the end effector. Using the cable band avoids the risk of drive cable derailment or displacement. Instead of the drive cable being wrapped about the input shaft, the cable band is wrapped around the input shaft. The geometry of the cable band presents little or no risk of derailment from the input shaft and/or any idler pulley that may be used to redirect the cable band. Moreover, the cable band may also be a type of constant force spring that helps maintain a minimum level of force (resistance) on the drive cable, which helps prevent the drive cable from slackening during operation.

Figure 1:
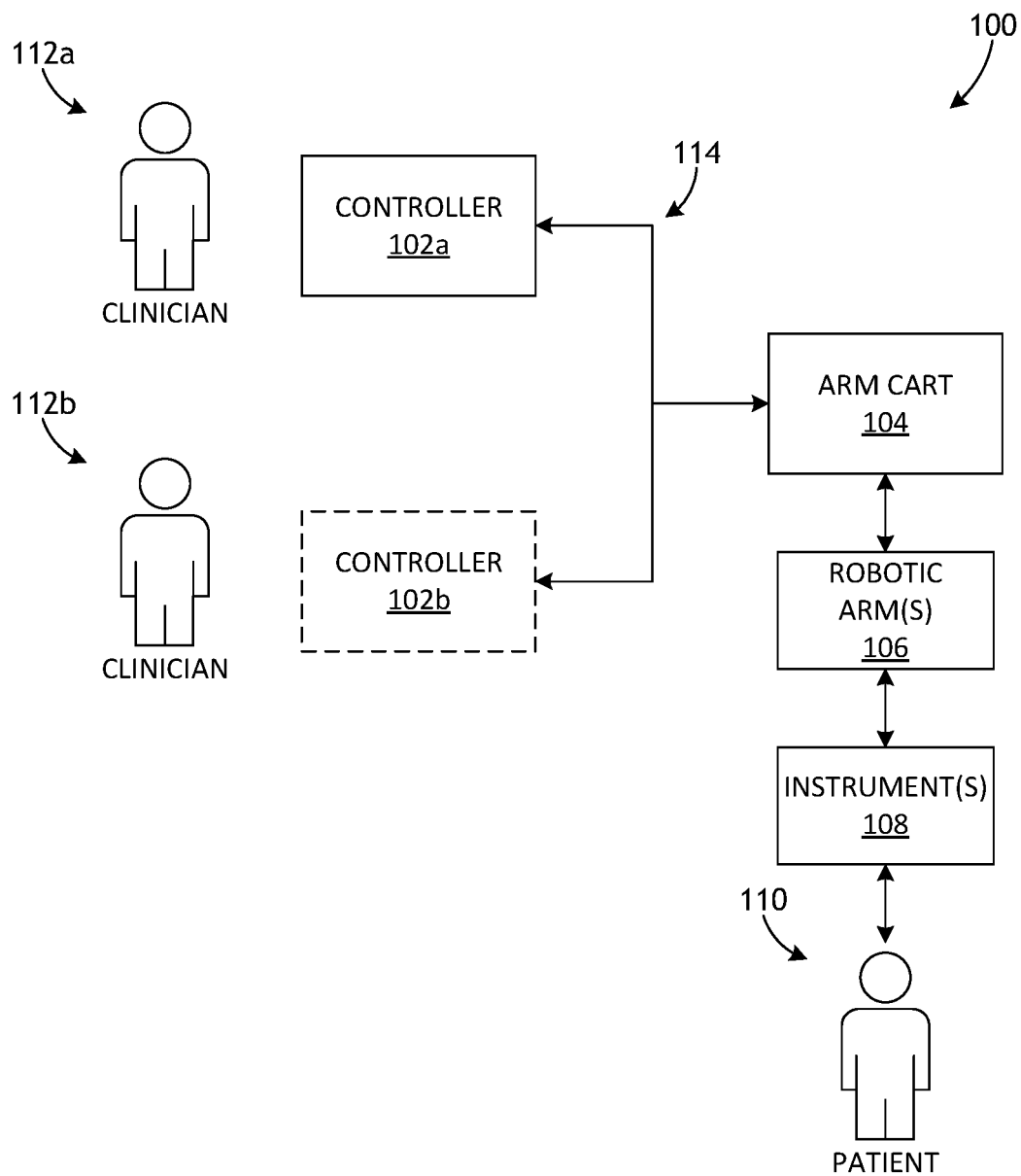
FIG. 1 is a block diagram of an example robotic surgical system that may incorporate some or all of the principles of the present disclosure.

FIGS. 1-5 illustrate the structure and operation of example robotic surgical systems and components thereof. FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient 110. Operation of the arm cart 104, including the arms 106 and instruments 108 may be directed by a clinician 112a (e.g., a surgeon) from the master controller 102a.

In some embodiments, a second master controller 102b (shown in dashed lines) operated by a second clinician 112b may also direct operation of the arm cart 104 in conjunction with the first clinician 112a. In such embodiments, for example, each clinician 112a,b may control different arms 106 of the arm cart 104 or, in some cases, complete control of the arm cart 104 may be passed between the clinicians 112a,b. In some embodiments, additional arm carts (not shown) may be utilized on the patient 110, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
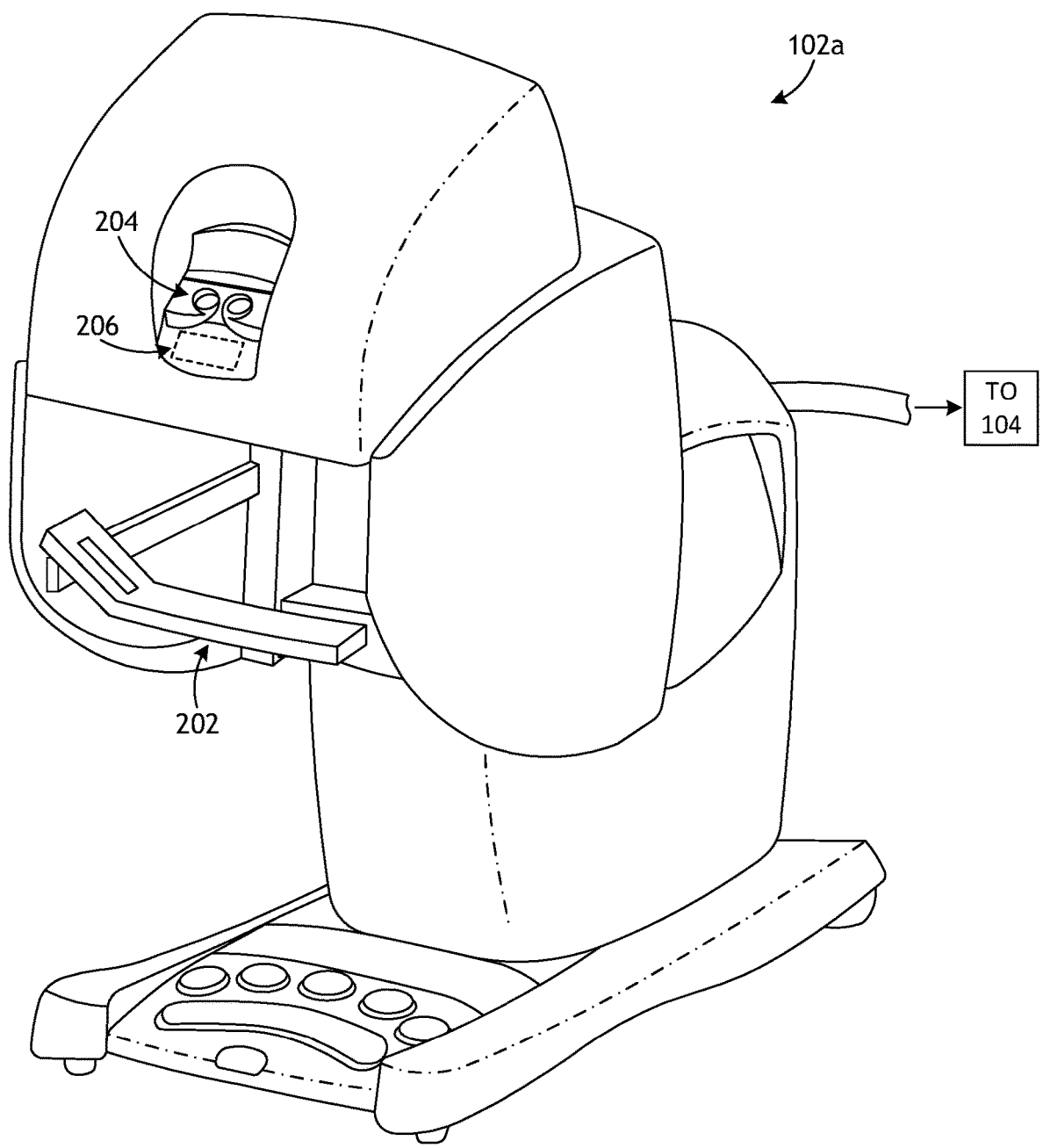
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician 112a of FIG. 1) and manipulated in space while the surgeon views the procedure via a stereo display 204. The master controllers 202 generally comprise manual input devices designed to move in multiple degrees of freedom, and which often further have an actuatable handle for actuating a surgical instrument (e.g., the surgical instrument(s) 108 of FIG. 1), for example, for opening and closing opposing jaws, applying an electrical potential to an electrode, or the like.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
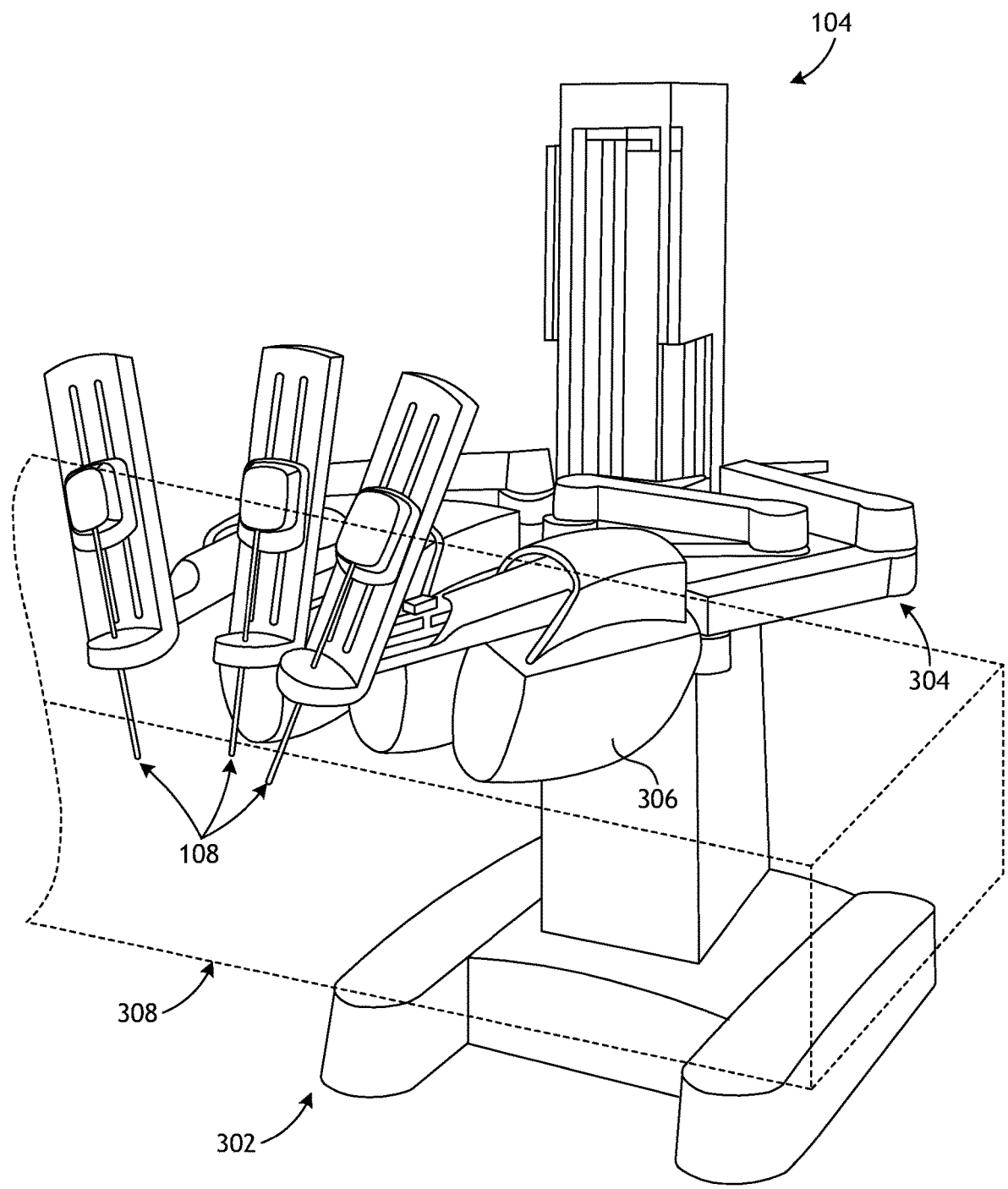
FIG. 3 depicts an example embodiment of the robotic arm cart of FIG. 1 used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of manually articulatable linkages, generally referred to as set-up joints 304, and a robotic manipulator 306. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 104.

The cart 104 will generally have dimensions suitable for transporting the cart 104 between operating rooms. The cart 104 may be configured to typically fit through standard operating room doors and onto standard hospital elevators. In some embodiments, the cart 104 may include a wheel system (or other transportation system) that allows the cart 104 to be positioned adjacent an operating table by a single attendant. In various embodiments, an automated reloading system including a base portion may be strategically located within a work envelope 308 of the robotic arm cart 104.

Figure 4:
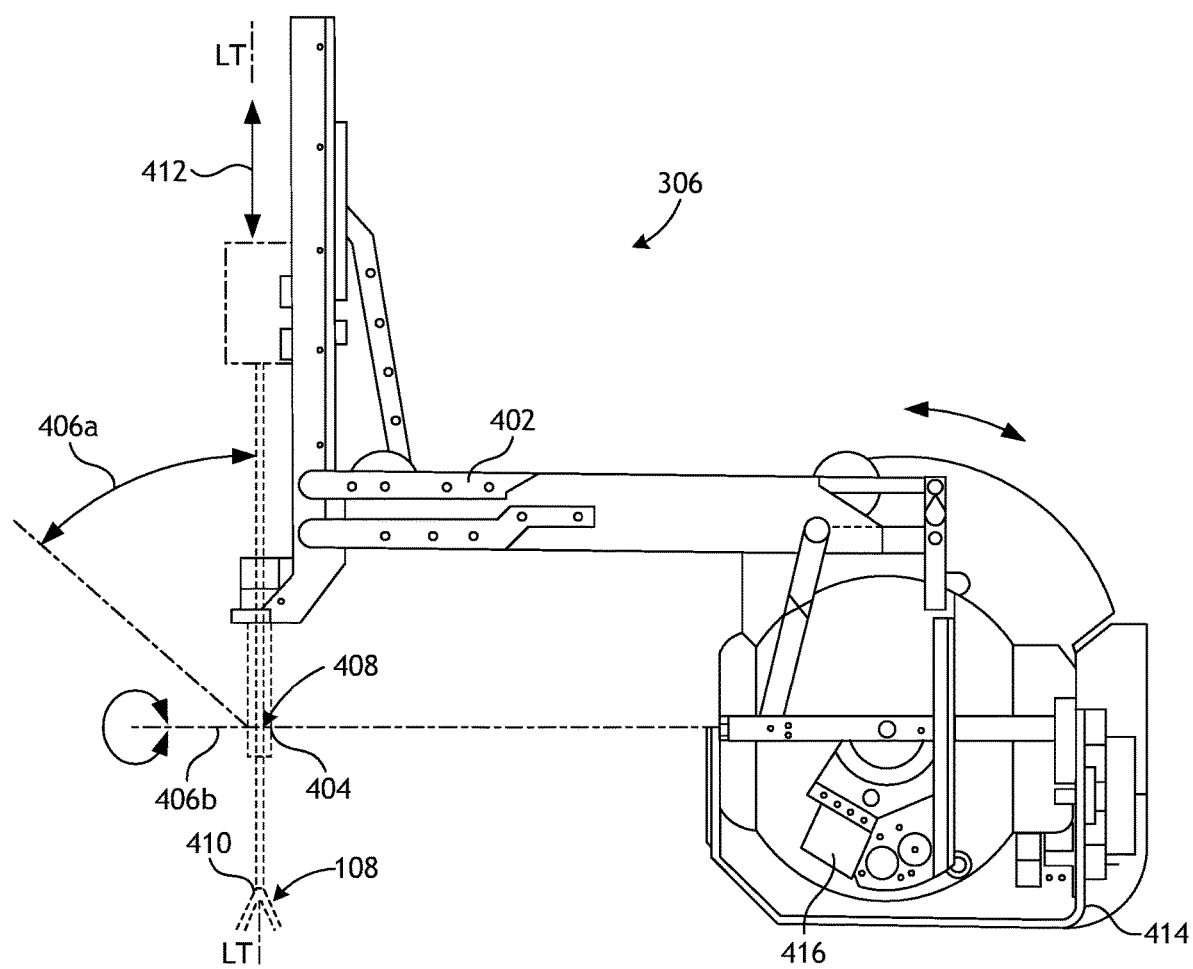
FIG. 4 is a side view schematic diagram of an example embodiment of the robotic manipulator of FIG. 3.

FIG. 4 is a side view schematic diagram of an example embodiment of the robotic manipulator 306. As illustrated, the robotic manipulator 306 may include linkage 402 that constrains movement of the surgical instrument 108 coupled thereto. The linkage 402 includes rigid links coupled by rotational joints in a parallelogram arrangement so that the surgical instrument 108 rotates around a point 404 in space.

The parallelogram arrangement constrains rotation to pivoting about a first axis 406a, referred to as the "pitch axis." The links supporting the parallelogram linkage 402 are pivotally mounted to set-up joints 304 (FIG. 3) so that the surgical instrument 108 further rotates about a second axis 406b, referred to as the "yaw axis." The pitch and yaw axes 406a, 406b intersect at a remote center 408, which is aligned along a shaft 410 of the surgical instrument 108.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the tool driver 306 (arrow 412), the remote center 408 remains fixed relative to a base 414 of the tool driver 306. Hence, the entire tool driver 306 is generally moved to re-position the remote center 408.

The linkage 402 of the tool driver 306 is driven by a series of motors 416. These motors 416 actively move the linkage 402 in response to commands from a processor of a control system. The motors 416 may also be employed to manipulate the surgical instrument 108.

Figure 5:
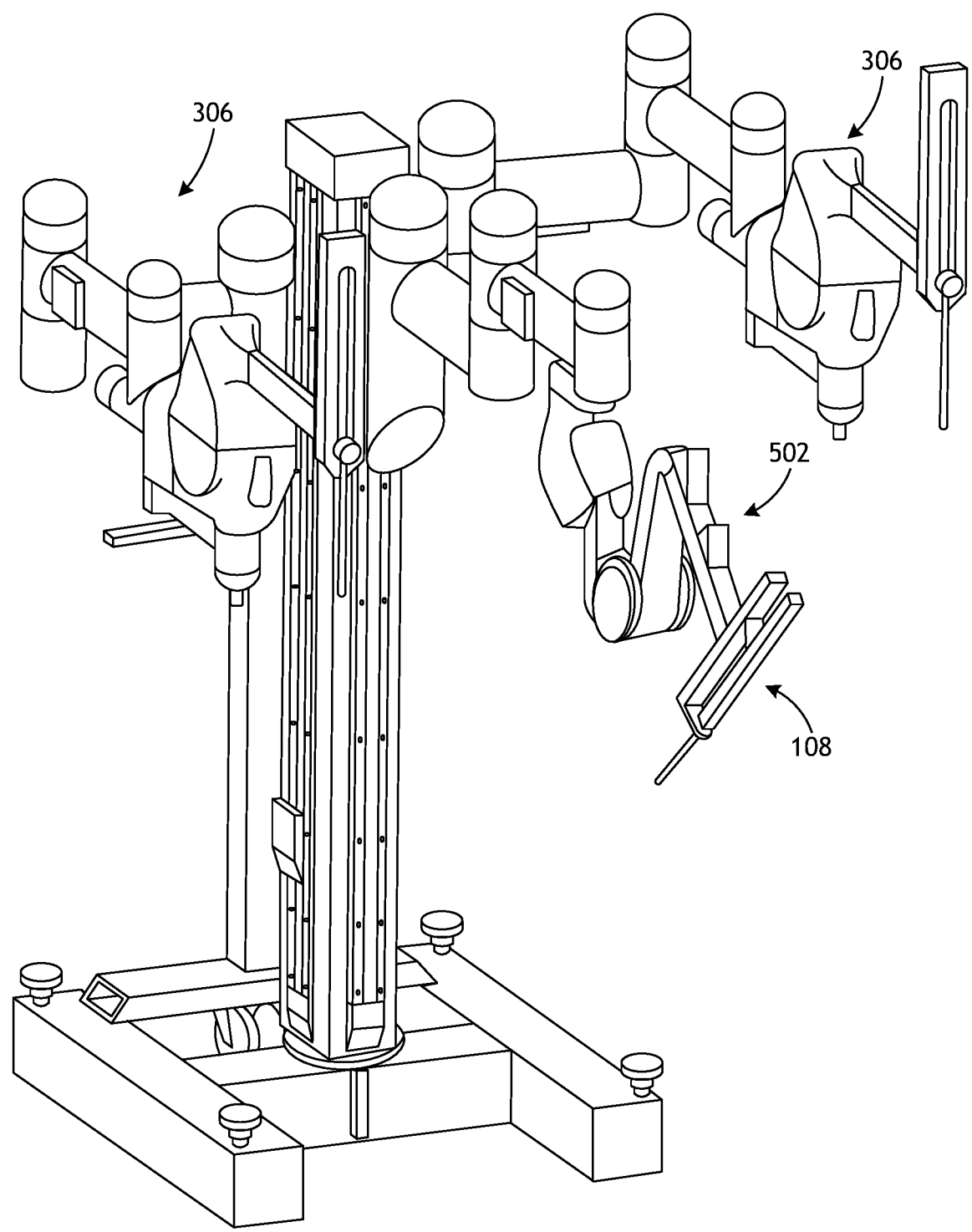
FIG. 5 is a perspective view of an alternative example robotic manipulator.

FIG. 5 is a perspective view of an alternative example robotic manipulator 502, used in conjunction with two robotic manipulators similar to the robotic manipulators 306 described in FIG. 4. As illustrated, a surgical instrument 108 is supported by the robotic manipulator 502 between the two robotic manipulators 306 generally described above. Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system is primarily described herein with reference to communication between the surgical instrument 108 and the master controller 102*a* (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 6:
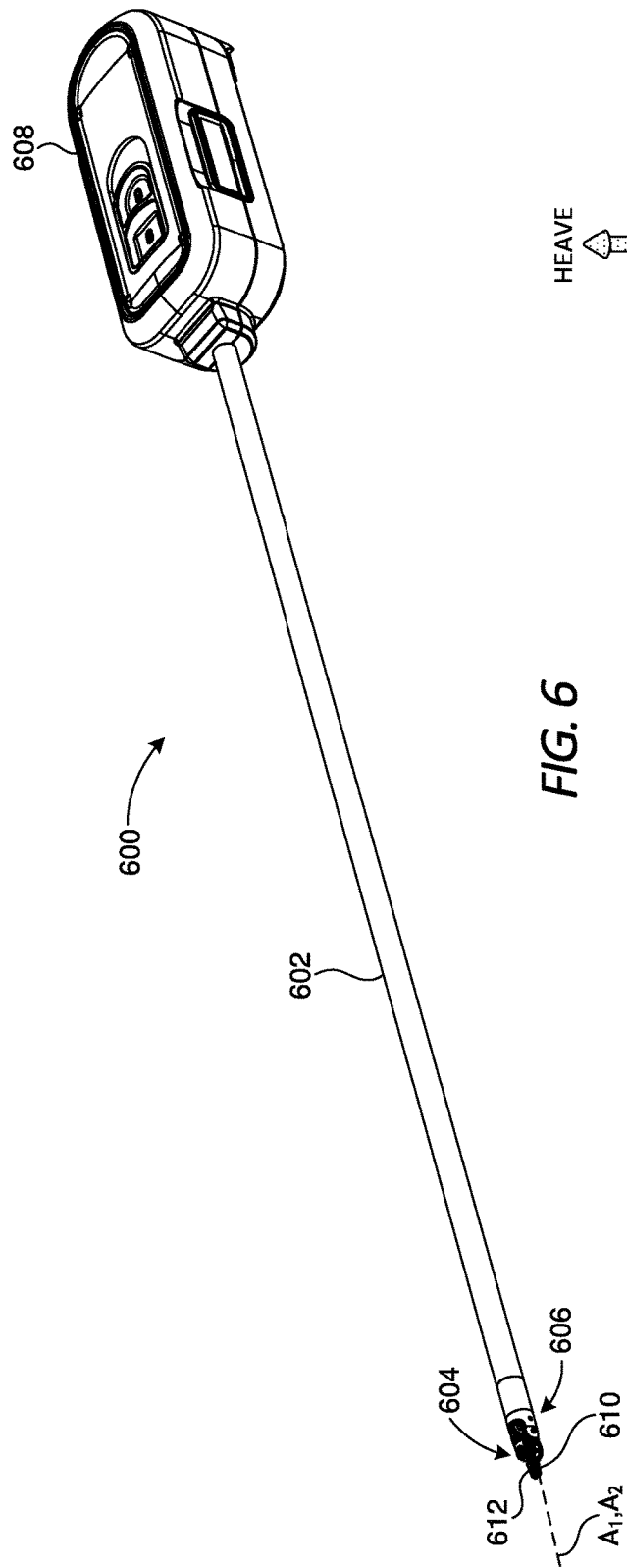
FIG. 6 is a side view of an example surgical tool that may incorporate some or all of the principles of the present disclosure.

FIG. 6 is a side view of an example surgical tool 600 that may incorporate some or all of the principles of the present disclosure. The surgical tool 600 may be the same as or similar to the surgical instrument(s) 108 of FIGS. 1 and 3-5) and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100.

As illustrated, the surgical tool 600 includes an elongate shaft 602, an end effector 604, a wrist 606 (alternately referred to as a "wrist joint") that couples the end effector 604 to the distal end of the shaft 602, and a drive housing 608 coupled to the proximal end of the shaft 602. In applications where the surgical tool 600 is used in conjunction with a robotic surgical system (e.g., the robotic surgical system 100 of FIG. 1), the drive housing 608 can include coupling features that releasably couple the surgical tool 600 to the robotic surgical system. It will be appreciated, however, that the principles of the present disclosure are equally applicable to surgical tools that are non-robotic and otherwise capable of manual manipulation.

The terms "proximal" and "distal" are defined herein relative to a robotic surgical system having an interface configured to mechanically and electrically couple the surgical tool 600 (e.g., the housing 608) to a robotic manipulator. The term "proximal" refers to the position of an element closer to the robotic manipulator and the term "distal" refers to the position of an element closer to the end effector 604 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 600, the end effector 604 is configured to move (pivot) relative to the shaft 602 at the wrist 606 to position the end effector 604 at desired orientations and locations relative to a surgical site. The housing 608 includes (contains) various mechanisms designed to control operation of various features associated with the end effector 604 (e.g., clamping, firing, rotation, articulation, energy delivery, etc.). In at least some embodiments, the shaft 602 (and hence the end effector 604 coupled thereto) is configured to rotate about a longitudinal axis $A_1$ of the shaft 602. In such embodiments, at least one of the mechanisms included (housed) in the housing 608 is configured to control rotational movement of the shaft 602 about the longitudinal axis $A_1$.

The surgical tool 600 can have any of a variety of configurations capable of performing at least one surgical function. For example, the surgical tool 600 may include, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the surgical tool 600 may be configured to apply energy to tissue, such as radiofrequency (RF) energy.

The shaft 602 is an elongate member extending distally from the housing 608 and has at least one lumen extending therethrough along its axial length. In some embodiments, the shaft 602 may be fixed to the housing 608, but could alternatively be rotatably mounted to the housing 608 to allow the shaft 602 to rotate about the longitudinal axis $A_1$. In yet other embodiments, the shaft 602 may be releasably coupled to the housing 608, which may allow a single housing 608 to be adaptable to various shafts having different end effectors.

The end effector 604 can have a variety of sizes, shapes, and configurations. In the illustrated embodiment, the end effector 604 includes opposing jaws 610, 612 configured to move (articulate) between open and closed positions. Accordingly, the end effector 604 can comprise, but is not limited to, a tissue grasper, a clip applier, scissors, a needle driver, a babcock including a pair of opposed grasping jaws, etc. One or both of the jaws 610, 612 may be configured to pivot at the wrist 606 to articulate the end effector 604 between the open and closed positions.

Figure 7:
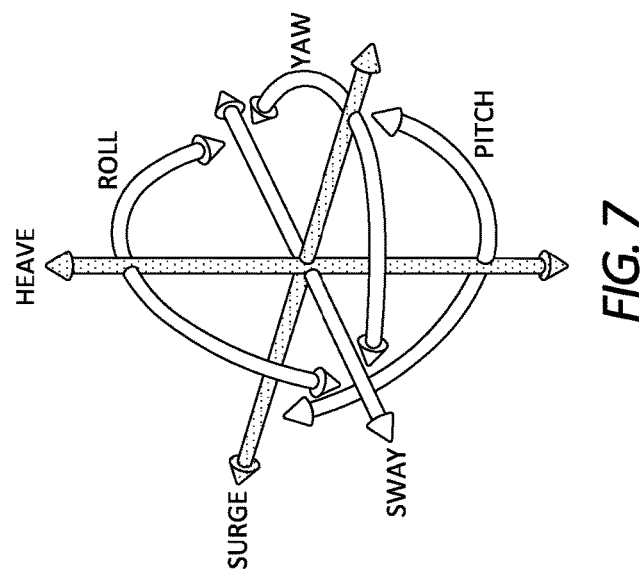
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The wrist 606 can have any of a variety of configurations. In general, the wrist 606 comprises a joint configured to allow pivoting movement of the end effector 604 relative to the shaft 602. The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 includes a plurality of drive cables (obscured in FIG. 6) that form part of a cable driven motion system configured to facilitate movement (articulation) of the end effector 604 relative to the shaft 602. Moving the drive cables moves the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. Due factors such as manufacturing tolerance and precision of measurement devices, the end effector 604 may not be at a precise zero angle relative to the shaft 602 in the unarticulated position, but nevertheless be considered "substantially aligned" thereto. In the articulated position, the longitudinal axes $A_1$, $A_2$ would be angularly offset from each other such that the end effector 604 is at a non-zero angle relative to the shaft 602.

Figure 8:
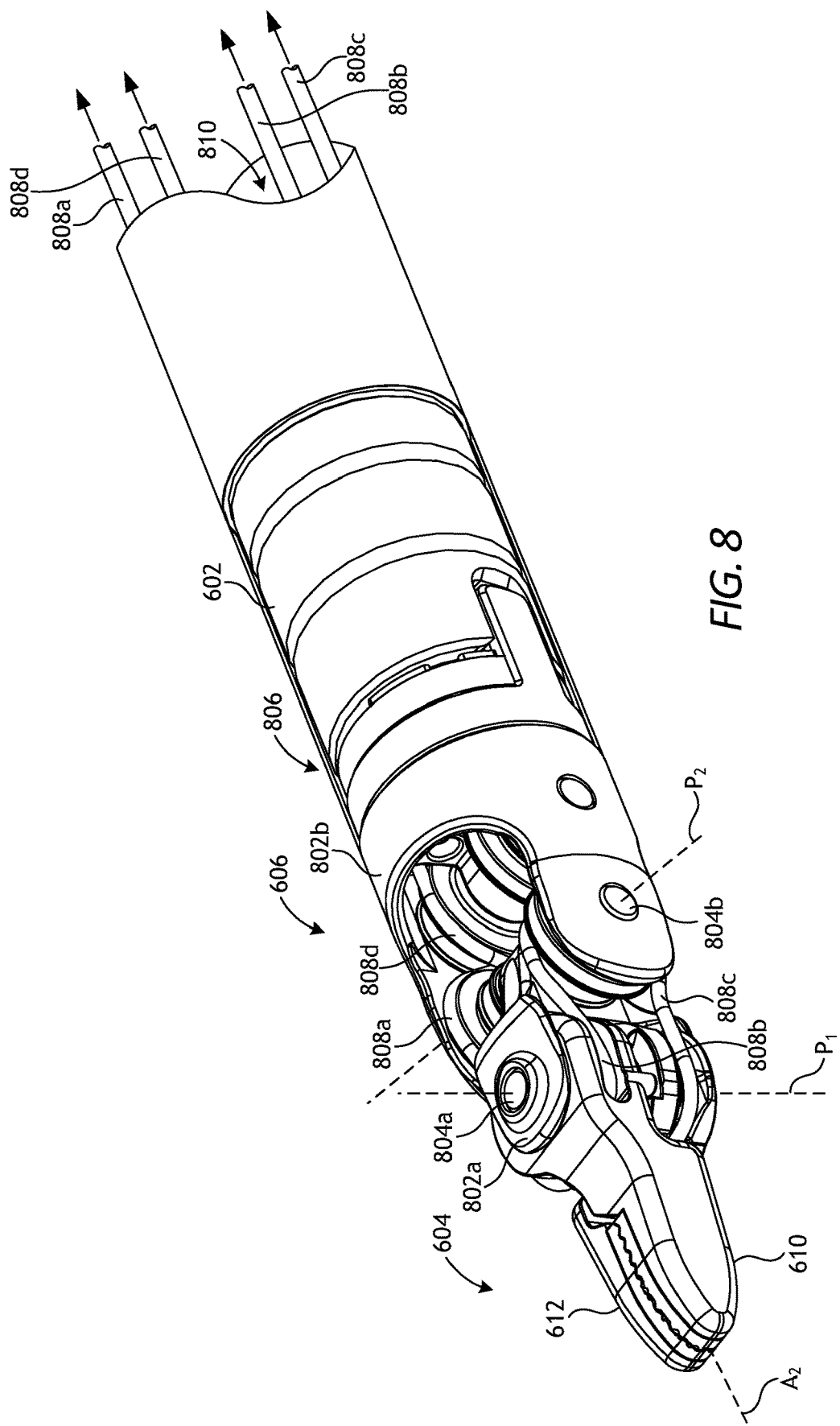
FIG. 8 is an enlarged isometric view of the distal end of the surgical tool of FIG. 1.

FIG. 8 is an enlarged isometric view of the distal end of the surgical tool 600 of FIG. 6. More specifically, FIG. 8 depicts enlarged views of the end effector 604 and the wrist 606, with the end effector 604 in the unarticulated position where the jaws 610, 612 are closed. The wrist 606 operatively couples the end effector 604 to the shaft 602. To accomplish this, the wrist 606 includes a distal clevis 802a and a proximal clevis 802b. The end effector 604 (i.e., the jaws 610, 612) is rotatably mounted to the distal clevis 802a at a first axle 804a, the distal clevis 802a is rotatably mounted to the proximal clevis 802b at a second axle 804b, and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604. In the illustrated embodiment, the jaws 610, 612 are mounted at the first pivot axis $P_1$, thereby allowing the jaws 610, 612 to pivot relative to each other to open and close the end effector 604 or alternatively pivot in tandem to articulate the orientation of the end effector 604.

A plurality of drive cables, shown as drive cables 808a, 808b, 808c, and 808d, extend longitudinally within a lumen 810 defined by the shaft 602 and pass through the wrist 606 to be operatively coupled to the end effector 604. The drive cables 808a-d form part of the cable driven motion system briefly described above, and may be referred to and otherwise characterized as cables, bands, lines, cords, wires, ropes, strings, twisted strings, elongate members, etc. The drive cables 808a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 810 can be a single lumen, as illustrated, or can alternatively comprise a plurality of independent lumens that each receive one or more of the drive cables 808a-d.

The drive cables 808a-d extend proximally from the end effector 604 to the drive housing 608 (FIG. 6) where they are operatively coupled to various actuation mechanisms or devices housed (contained) therein to facilitate longitudinal movement (translation) of the drive cables 808a-d within the lumen 810. Selective actuation of all or a portion of the drive cables 808a-d causes the end effector 604 (e.g., one or both of the jaws 610, 612) to articulate (pivot) relative to the shaft 602. More specifically, selective actuation causes a corresponding drive cable 808a-d to translate longitudinally within the lumen 810 and thereby cause pivoting movement of the end effector 604. One or more drive cables 808a-d, for example, may translate longitudinally to cause the end effector 604 to articulate (e.g., both of the jaws 610, 612 angled in a same direction), to cause the end effector 604 to open (e.g., one or both of the jaws 610, 612 move away from the other), or to cause the end effector 604 to close (e.g., one or both of the jaws 610, 612 move toward the other).

Moving the drive cables 808a-d can be accomplished in a variety of ways, such as by triggering an associated actuator or mechanism operatively coupled to or housed within the drive housing 608 (FIG. 6). Moving a given drive cable 808a-d constitutes applying tension (i.e., pull force) to the given drive cable 808a-d in a proximal direction, which causes the given drive cable 808a-d to translate and thereby cause the end effector 604 to move (articulate) relative to the shaft 602.

The wrist 606 includes a first plurality of pulleys 812a and a second plurality of pulleys 812b, each configured to interact with and redirect the drive cables 808a-d for engagement with the end effector 604. The first plurality of pulleys 812a is mounted to the proximal clevis 802b at the second axle 804b and the second plurality of pulleys 812b is also mounted to the proximal clevis 802b but at a third axle 804c located proximal to the second axle 804b. The first and second pluralities of pulleys 812a,b cooperatively redirect the drive cables 808a-d through an "S" shaped pathway before the drive cables 808a-d are operatively coupled to the end effector 604.

In at least one embodiment, one pair of drive cables 808a-d is operatively coupled to each jaw 610, 612 and configured to "antagonistically" operate the corresponding jaw 610, 612. In the illustrated embodiment, for example, the first and second drive cables 808a,b may be coupled at the first jaw 610, and the third and fourth drive cables 808c,d may be coupled at the second jaw 612. Actuation of the first drive cable 808a acts on and pivots the first jaw 610 about the first pivot axis $P_1$ toward the open position. In contrast, actuation of the second drive cable 808b also acts on and pivots the first jaw 610 about the first pivot axis $P_1$ in the opposite direction and toward the closed position. Similarly, actuation of the third drive cable 808c acts and pivots the second jaw 612 about the first pivot axis $P_1$ toward the open position, while actuation of the fourth drive cable 808d also acts on but pivots the second jaw 612 about the first pivot axis $P_1$ in the opposite direction and toward the closed position.

Accordingly, the drive cables 808a-d may be characterized or otherwise referred to as "antagonistic" cables that cooperatively (yet antagonistically) operate to cause relative or tandem movement of the first and second jaws 610, 612. When the first drive cable 808a is actuated (moved), the second drive cable 808b naturally follows as coupled to the first drive cable 808a, and vice versa. Similarly, when the third drive cable 808c is actuated, the fourth drive cable 808d naturally follows as coupled to the third drive cable 808c, and vice versa.

Moreover, coordinated actuation of the drive cables 808a-d may also articulate the end effector 604 about the second pivot axis $P_2$. Consequently, the end effector 604 can articulate with multiple degrees of freedom, e.g., a degree of freedom by articulating about the first pivot axis $P_1$ and another degree of freedom by articulating about the second pivot axis $P_2$. The wrist 606 in this embodiment is pivotable about the second pivot axis $P_2$ in a single plane, e.g., in one of pitch and yaw, and the end effector 604 is pivotable about the first pivot axis $P_1$ in a single, different plane, e.g., the other of pitch and yaw.

Figure 9:
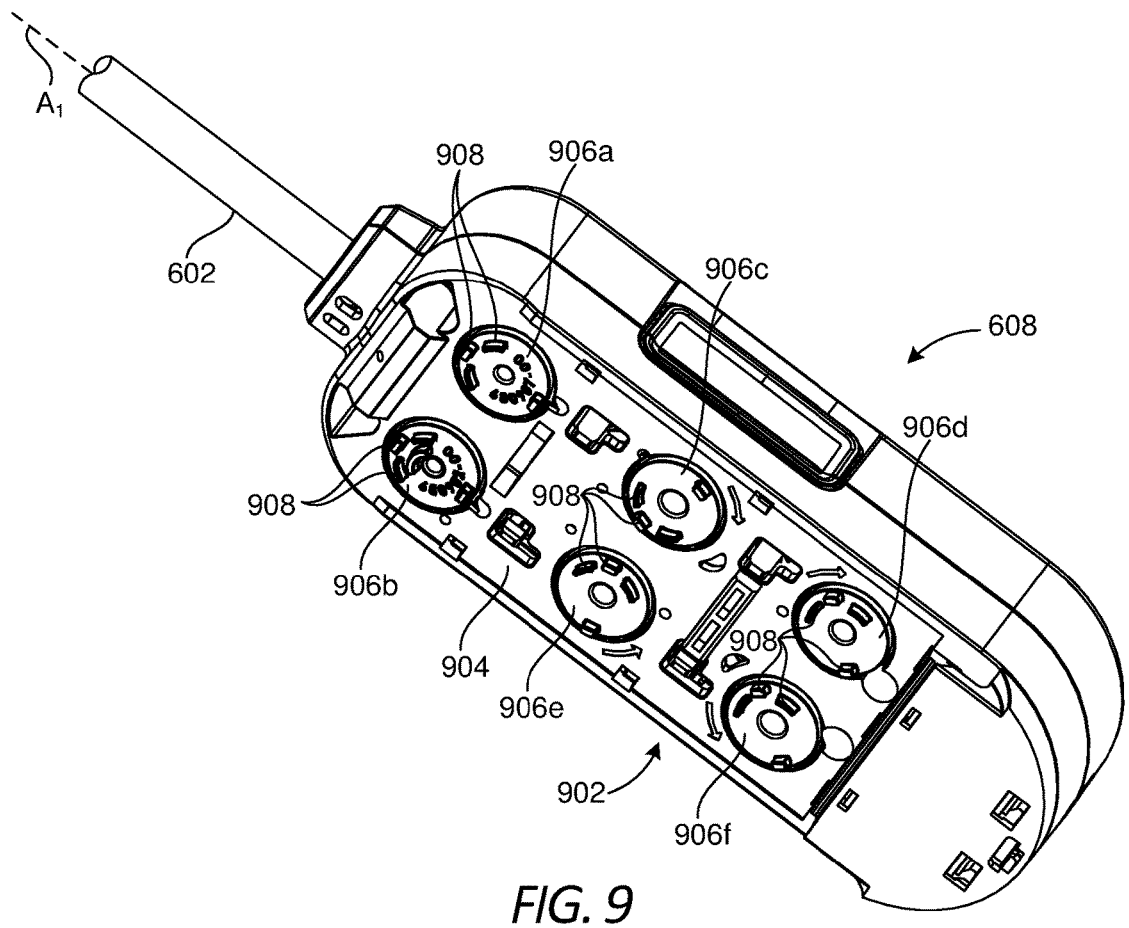
FIG. 9 is a bottom view of the drive housing of the surgical tool of FIG. 6.

FIG. 9 is a bottom view of the drive housing 608, according to one or more embodiments. As illustrated, the drive housing 608 (alternately referred to as a "puck") may include a tool mounting portion 902 used to operatively couple the drive housing 608 to a tool driver of a robotic manipulator (e.g., the robotic manipulators 306, 502 of FIGS. 3 and 5, respectively). The tool mounting portion 902 may releasably couple the drive housing 608 to a tool driver in a variety of ways, such as by clamping thereto, clipping thereto, or slidably mating therewith. In some embodiments, the tool mounting portion 902 may include an array of electrical connecting pins, which may be coupled to an electrical connection on the mounting surface of the tool driver. While the tool mounting portion 902 is described herein with reference to mechanical, electrical, and magnetic coupling elements, it should be understood that a wide variety of telemetry modalities might be used, including infrared, inductive coupling, or the like.

The tool mounting portion 902 includes and otherwise provides an interface 904 configured to mechanically, magnetically, and/or electrically couple the drive housing 608 to the tool driver. As illustrated, the interface 904 includes and supports a plurality of inputs, shown as drive inputs 906a, 906b, 906c, 906d, 906e, and 906f. In at least one embodiment, each drive input 906a-f comprises a rotatable disc configured to align with and couple to a corresponding actuator of a given tool driver. Moreover, each drive input 906a-f provides or defines one or more surface features 908 configured to align with mating surface features provided on the corresponding actuator. The surface features 908 can include, for example, various protrusions and/or indentations that facilitate a mating engagement. In some embodiments, some or all of the drive inputs 906a-f may include one surface feature 908 that is positioned closer to an axis of rotation of the associated drive input 906a-f than the other surface feature(s) 908. This may help to ensure positive angular alignment of each drive input 906a-f.

In some embodiments, actuation of the first drive input 906a may be configured to control rotation of the elongate shaft 602 about its longitudinal axis $A_1$. The elongate shaft 602 may be rotated clockwise or counter-clockwise depending on the rotational actuation of the first drive input 906a. In some embodiments, actuation of the second drive input 906b may be configured to control a lockout mechanism (alternately referred to as a deadbolt), which locks the end effector 604 (FIGS. 6 and 8) in a predetermined pose or position. In some embodiments, actuation of the third, fourth, fifth, and sixth drive inputs 906c-f may be configured to operate movement (axial translation) of the drive cables 808a-d (FIG. 8), respectively, which results in the articulation of the end effector 604. Each of the drive inputs 906a-f may be actuated based on user inputs communicated to a tool driver coupled to the interface 904, and the user inputs may be received via a computer system incorporated into the robotic surgical system.

Figure 10:
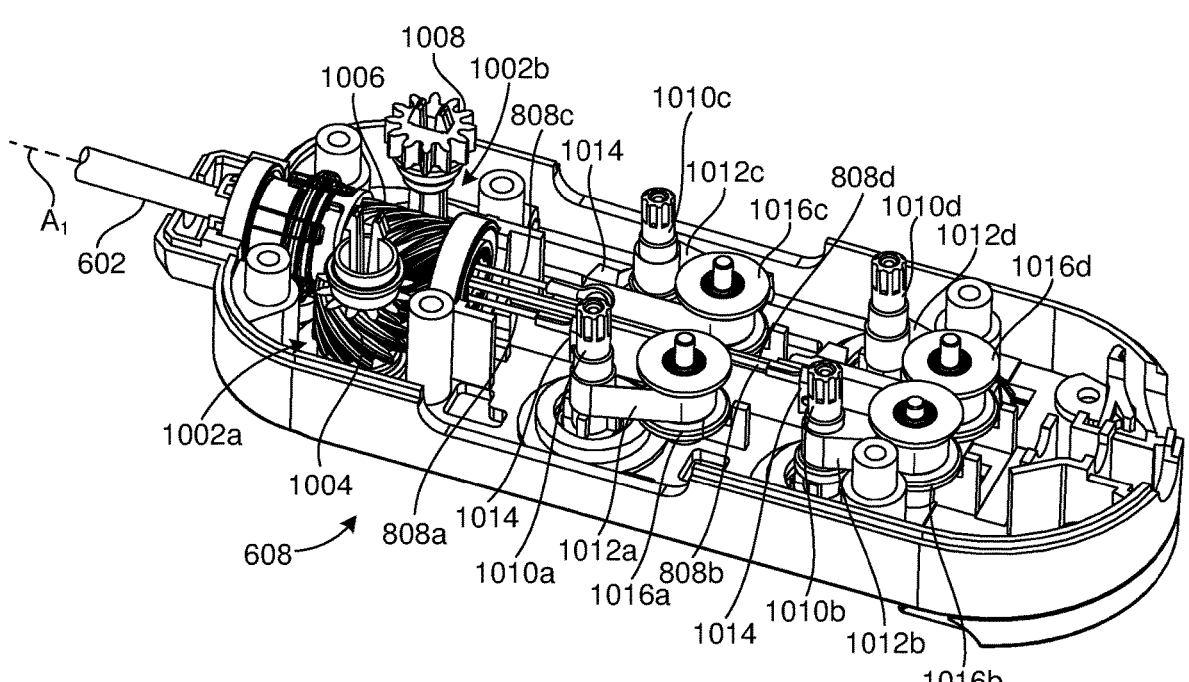
FIG. 10 is an isometric exposed view of the interior of the drive housing of the surgical tool of FIG. 6.

FIG. 10 is an isometric exposed view of the interior of the drive housing 608, according to one or more embodiments. Several component parts that may be otherwise contained within the drive housing 608 are not shown in FIG. 10 to enable discussion of the depicted component parts. As illustrated, a first capstan 1002a and a second capstan 1002b are contained (housed) within the drive housing 608. The first capstan 1002a may be operatively coupled to or extend from the first drive input 906a (FIG. 9), and the second capstan 1002b may be operatively coupled to or extend from the second drive input 906b (FIG. 9). Accordingly, actuation of the first drive input 906a results in rotation of the first capstan 1002a and actuation of the second drive input 906b results in rotation of the second capstan 1002b.

A spiral worm drive gear 1004 is coupled to or forms part of the first capstan 1002a. The spiral worm drive gear 1004 may be configured to mesh and interact with a driven gear 1006 secured within the drive housing 608 and operatively coupled to the shaft 602 such that rotation of the driven gear 1006 correspondingly rotates the shaft 602. Accordingly, rotation of the spiral worm drive gear 1004 (via actuation of the first drive input 906a of FIG. 9) will drive the driven gear 1006 and thereby control rotation of the elongate shaft 602 about the longitudinal axis $A_1$.

In some embodiments, the second capstan 1002b may have a pinion gear 1008 coupled thereto and configured to mesh and interact with a rack (not shown) contained within the drive housing 608. The rack may be operatively coupled to a lockout mechanism that is movable to lock the end effector 604 (FIGS. 6 and 8) in a predetermined pose or position. Accordingly, rotation of the pinion gear 1008 (via actuation of the second drive input 906b of FIG. 9) will control the lockout mechanism and thereby lock and unlock the end effector 604 when desired.

The drive housing 608 further contains or houses a first input shaft 1010a, a second input shaft 1010b, a third input shaft 1010c, and a fourth input shaft 1010d. In the illustrated embodiment, the first input shaft 1010a is operatively coupled to or extends from the third drive input 906c (FIG. 9), the second input shaft 1010b is operatively coupled to or extends from the fourth drive input 906d (FIG. 9), the third input shaft 1010c is operatively coupled to or extends from the fifth drive input 906e (FIG. 9), and the fourth input shaft 1010d is operatively coupled to or extends from the sixth drive input 906f (FIG. 9). Accordingly, actuation of the third drive input 906c results in rotation of the first input shaft 1010a, actuation of the fourth drive input 906d results in rotation of the second input shaft 1010b, actuation of the fifth drive input 906e results in rotation of the third input shaft 1010c, and actuation of the sixth drive input 906f results in rotation of the fourth input shaft 1010d. While four input shafts 1010a-d are depicted in FIG. 10, it is contemplated herein to include more or less than four, without departing from the scope of the disclosure.

Each input shaft 1010a-d is operatively coupled to a corresponding one of the drive cables 808a-d. More specifically, a first cable band 1012a extends between and operatively couples the first input shaft 1010a and the first drive cable 808a, a second cable band 1012b extends between and operatively couples the second input shaft 1010b and the second drive cable 808a, a third cable band 1012c extends between and operatively couples the first input shaft 1010a and the first drive cable 808a, and a fourth cable band 1012d extends between and operatively couples the first input shaft 1010a and the first drive cable 808a. In example operation, rotation of the first input shaft 1010a (via actuation of the third drive input 906c of FIG. 9) will correspondingly control movement of the first drive cable 808a via the first cable band 1012a; rotation of the second input shaft 1010b (via actuation of the fourth drive input 906d of FIG. 9) will correspondingly control movement of the second drive cable 808b via the second cable band 1012b; rotation of the third input shaft 1010c (via actuation of the fifth drive input 906e of FIG. 9) will correspondingly control movement of the third drive cable 808c via the third cable band 1012c; and rotation of the fourth input shaft 1010d (via actuation of the sixth drive input 906f of FIG. 9) will correspondingly control movement of the fourth drive cable 808d via the fourth cable band 1012d.

As used herein, the term "operatively coupled" can refer to a direct or indirect coupling engagement between two structural component parts. In at least one embodiment, for example, the cable bands 1012a-d may not be directly coupled to the corresponding drive cables 808a-d. Rather, in some embodiments, each cable band 1012a-d may be directly coupled to a corresponding hypotube (or another type of rigid or semi-rigid, elongate member), which indirectly couples the cable band 1012a-d to an associated drive cable 808a-d, without departing from the scope of the disclosure. Accordingly, stating that the cable bands 1012a-d extend between and operatively couple a given input shaft 1010a-d to a corresponding drive cable 808a-d may 1) refer to the cable band 1012a-d directly coupling to the corresponding drive cable 808a-d or 2) refer to a hypotube or like structure that is directly coupled to the corresponding drive cable 808a-d. Consequently, the drive cables 808a-d referenced in FIG. 10 may alternatively be referenced as hypotubes that are connected to the drive cables 808a-d, without departing from the scope of the disclosure.

As discussed in more detail below, each cable band 1012a-d may comprise a ribbon or strip of material that exhibits a height that is greater than its cross-sectional thickness. In some embodiments, one end of each cable band 1012a-d is wrapped one or more times about an associated input shaft 1010a-d, and the other end of each cable band 1012a-d is coupled to a corresponding drive cable 808a-d via a connector 1014.

In some embodiments, each cable band 1012a-d may comprise a constant force spring that exerts a known and constant torque resistance over its range of motion. Each cable band 1012, for example, may comprise a rolled ribbon of spring steel that is relaxed when fully rolled up. In other embodiments, one or more of the cable bands 1012 may comprise a ribbon or strip of material made of aluminum, titanium, a polymer, an elastomer, a fiber mesh, or any combination of the foregoing. As it unrolls from the associated input shaft 1010a-d during operation, the cable band 1012a-d may provide a constant torque force that helps prevent the drive cables 808a-d from relaxing (slackening). Because the geometry of the cable bands 1012a-d remains nearly constant as the cable bands 1012a-d unroll, the resulting resistance force is nearly or entirely constant. This is in contrast to typical torsion springs, which tend to increase in resistance over their range of motion.

In some embodiments, one or more of the cable bands 1012a-d may be routed at least partially around an idler pulley rotatably mounted within the drive housing 608. More specifically, the first cable band 1012a may be routed around a first idler pulley 1016a as it extends between the first input shaft 1010a and the first drive cable 808a; the second cable band 1012b may be routed around a second idler pulley 1016b as it extends between the second input shaft 1010b and the second drive cable 808b; the third cable band 1012c may be routed around a third idler pulley 1016c as it extends between the third input shaft 1010c and the third drive cable 808c; and the fourth cable band 1012d may be routed around a fourth idler pulley 1016d as it extends between the fourth input shaft 1010d and the fourth drive cable 808d. Each idler pulley 1016a-d may be arranged within the drive housing 608 such that the corresponding cable band 1012a-d feeds the connected drive cable 808a-d directly into the elongate shaft 602. In other embodiments, however, one or more additional idler pulleys may be employed to redirect the cable bands 1012a-d and/or drive cables 808a-d, without departing from the scope of the disclosure.

The cable bands 1012a-d may prove advantageous in mitigating or avoiding the risk of drive cable derailment or displacement. In other surgical tools, the drive cables themselves are often wrapped multiple times about the input shaft (e.g., a drive cable capstan), sometimes helically such that the position of the drive cable changes elevation as it extends about the circumference of the input shaft. The drive cables are also often wrapped around an adjacent idler pulley, sometimes multiple times. Such surgical tools present multiple locations that risk derailment or displacement of the drive cables during operation. In contrast, the geometry of the presently disclosed cable bands 1012a-d, which form a ribbon or strip-like structure, present little or no risk of derailing from the corresponding input shafts 1010a-d and/or idler pulleys 1016a-d. The ribbon or strip material of the cable bands 1012a-d exhibit rigidity that stays in a single plane.

The cable bands 1012a-d may also prove advantageous in helping to maintain a minimum level of force (resistance) on a corresponding drive cable 808a-d, which helps prevent the corresponding drive cable 808a-d from slackening during operation. More specifically, in embodiments where the cable bands 1012a-d comprise constant force springs, any torque resistance exhibited by the cable bands 1012a-d will be transmitted to and otherwise assumed by the corresponding drive cable 808a-d. As each input shaft 1010a-d is actuated to move a corresponding drive cable 808a-d, the associated cable band 1012a-d either unrolls from or retracts back onto the associated input shaft 1010a-d and simultaneously provides a known and constant torque resistance across its entire range of motion in either direction. If any slack develops in the drive cables 808a-d during operation (or while cleaning the tool), the geometry of the corresponding cable band 1012a-d constantly removes such slack as it is continuously biased to the associated input shaft 1010a-d. As a result, a constant torque is assumed by the corresponding drive cable 808a-d, which helps keeps the corresponding drive cable 808a-d taut at all times during operation.

Figure 11A:
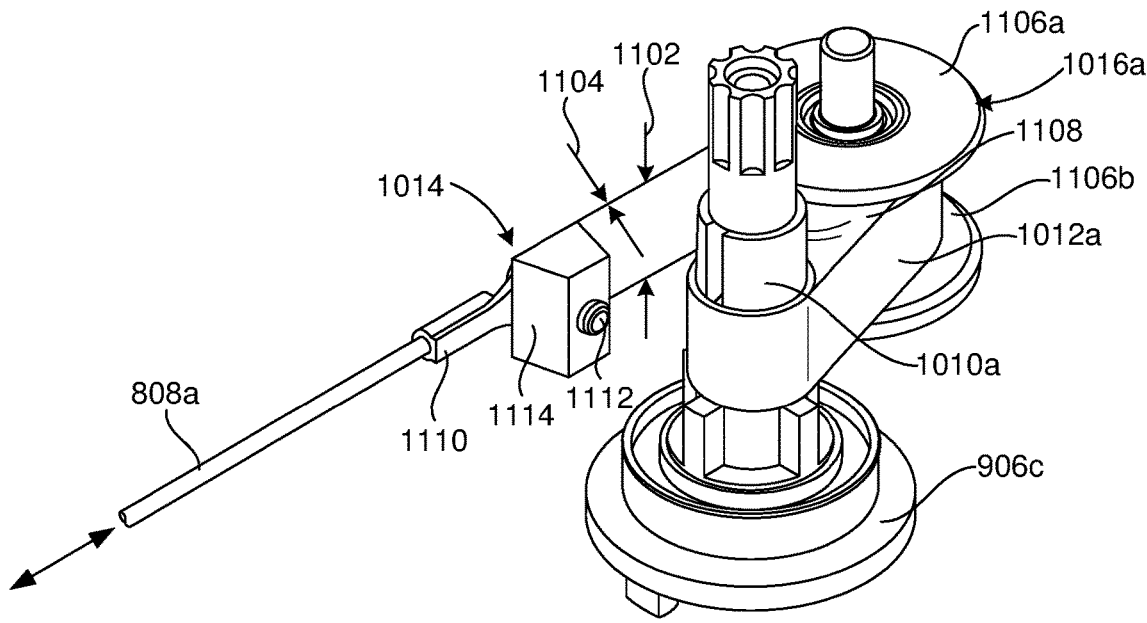
FIGS. 11A and 11B are opposing isometric side views of the first input shaft, the first cable band, and the first idler pulley cooperatively arranged for operation.
Figure 11B:
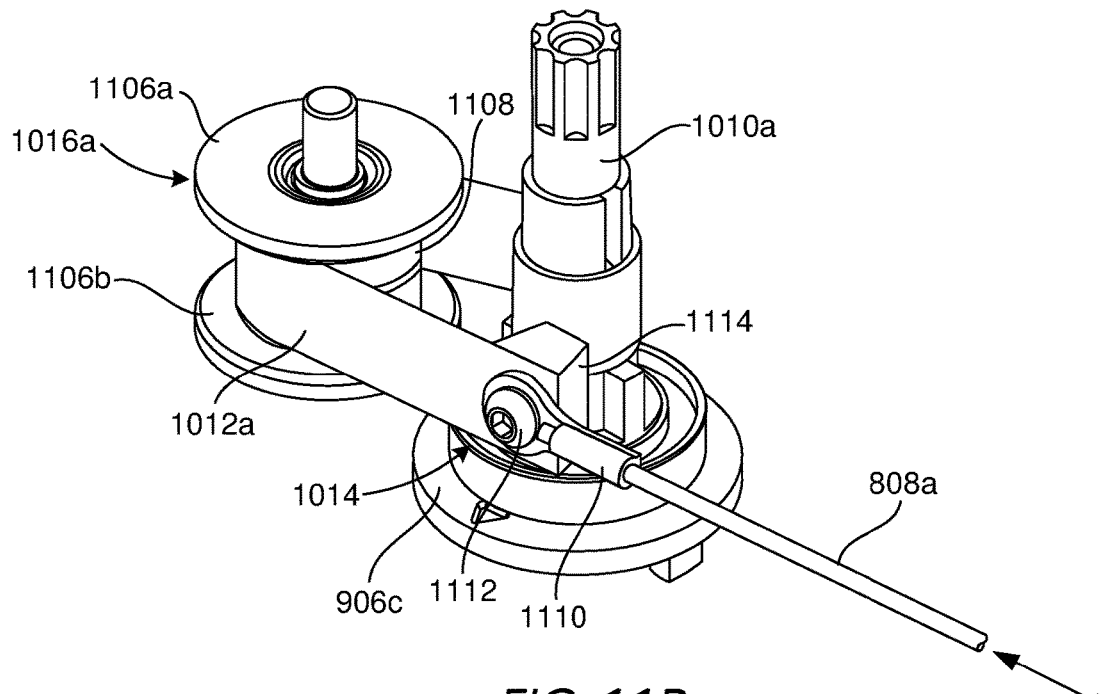

FIGS. 11A and 11B are opposing isometric side views of the first input shaft 1010a, the first cable band 1012a, and the first idler pulley 1016a cooperatively arranged for operation, according to one or more embodiments. While discussing specifics and details of the first input shaft 1010a, the first cable band 1012a, and the first idler pulley 1016a, the following description is equally applicable to any of the input shafts 1010a-d, cable bands 1012a-d, and idler pulleys 1016a-d described herein with reference to FIG. 10. Accordingly, the following discussion is equally applicable to operation of the second, third, and fourth input shafts 1010b,c,d, cable bands 1012b,c,d, and idler pulleys 1016b,c,d, respectively.

As mentioned above, the first input shaft 1010a is operatively coupled to or extends from the third drive input 906c, and actuation of the third drive input 906c correspondingly rotates the first input shaft 1010a. Moreover, as also mentioned above, the first cable band 1012a extends between and operatively couples the first drive cable 808a to the first input shaft 1010a. As illustrated, the first cable band 1012a may also be routed at least partially around the first idler pulley 1016a. Actuating the third drive input 906c rotates the first input shaft 1010a, which correspondingly moves the first cable band 1012a and thereby controls longitudinal movement of the first drive cable 808a in either longitudinal direction.

The first cable band 1012a may exhibit a height 1102 (FIG. 11A) and a thickness 1104 (FIG. 11A), where the height 1102 is much greater than the thickness 1104. In some embodiments, the height 1102 may be about 0.5 inches, and the thickness 1104 may be about 0.003 inches or more. Such dimensions, however, are stated herein as merely examples. Those skilled in the art will readily appreciate that the magnitude of the height 1102 and the thickness 1104 may assume a variety of dimensions, without departing from the scope of the disclosure. As illustrated, the first cable band 1012a may comprise a ribbon or strip of material. Suitable materials for the first cable band 1012a include, but are not limited to, steel (e.g., spring steel), a plastic, an elastomer, a woven structure, a composite material, a laminated material, or any combination thereof.

The first cable band 1012a may prove advantageous in mitigating or eliminating the risk of drive cable derailment or displacement. Since the first drive cable 808a does not wrap around or engage the first input shaft 1010a or the first idler pulley 1016a, the risk of drive cable derailment or displacement is effectively eliminated. Rather, the planar nature of the first cable band 1012a helps mitigate or avoid derailment of the first cable band 1012a from the first input shaft 1010a or the first idler pulley 1016a.

The first idler pulley 1016a comprises a free-spinning structure used to receive and redirect the first cable band 1012a from the first input shaft 1010a. In some embodiments, as illustrated, the first idler pulley 1016a may include upper and lower flanges 1106a and 1106b and a trough 1108 that extends between the upper and lower flanges 1106a,b. The first cable band 1012a may be received within the trough 1108 and the upper and lower flanges 1106a,b may help maintain the first cable band 1012a within the trough 1108 during operation.

The connector 1014 may be used to couple the first cable band 1012a to the first drive cable 808a such that movement of the first cable band 1012a correspondingly moves the first drive cable 808a. As mentioned above, however, it is also contemplated herein that the first drive cable 808a referenced in FIGS. 11A and 11B be replaced with a hypotube, which is coupled to the first drive cable at a distal end of the hypotube. Accordingly, in such embodiments, the connector 1014 may be used to couple the first cable band 1012a to a hypotube, which is directly coupled to the first drive cable 808a at the distal end of the hypotube, without departing from the scope of the disclosure.

Suitable forms of the connector 1014 include, but are not limited to, one or more mechanical fasteners, a snap-fit engagement between opposing ends of the first cable band 1012a to the first drive cable 808a, welding or adhesively attaching the first cable band 1012a to the first drive cable 808a, and any combination thereof.

In the illustrated embodiment, the connector 1014 includes a fisheye connector 1110 secured (e.g., crimped) to an end of the first drive cable 808a, a mechanical fastener 1112, and a nut 1114. The mechanical fastener 1112 in the present embodiment comprises a screw or a bolt with a threaded end. To assemble the connector 1014 and thereby couple the first cable band 1012a to the first drive cable 808a, the mechanical fastener 1112 (e.g., a screw or bolt) may be extended through an aperture (occluded) defined by the fisheye connector 1110. In some embodiments, the mechanical fastener 1112 may also be extended through an aperture (occluded) defined in the end of the first cable band 1012a. In other embodiments, however, tightening the connection 1114 over a portion of the first cable band 1012a may provide a sufficient connective force. The nut 1114 may then be threaded onto the end of the mechanical fastener 1112 and tightened.

As will be appreciated, the foregoing description of the connector 1014 is merely one example of the connector 104 and is shown for illustrative purposes only. Therefore, the foregoing description of the connector 1014 should not be considered limiting to the present disclosure. Indeed, the connector 1014 can assume a multitude of forms and designs in coupling the first cable band 1012a to the first drive cable 808a, without departing from the scope of the disclosure.

In embodiments where the first cable band 1012a comprises a constant force spring, the first cable band 1012a may also prove advantageous in helping maintain constant torque resistance on the first drive cable 808a, which helps prevent the first drive cable 808a from relaxing (e.g., slackening). More specifically, the first cable band 1012a either unrolls from or retracts back onto the first input shaft 1010a as the first input shaft 1010a rotates, and thereby provides a known and constant torque resistance across its entire range of motion in either angular direction of rotation. This constant torque resistance is assumed by the first drive cable 808a to keep the first drive cable 808a taut at all times during operation.

The constant resistance force provided by the first cable band 1012a may be especially advantageous for robotic surgical instruments, such as the surgical tool 600 of FIG. 6. Because the first cable band 1012a may provide a constant torque over its displacement, the force required from a robotic tool driver (e.g., the tool driver 306 of FIG. 3) need not be altered to adjust for changing torque resistance. In contrast, other surgical tools use torsion springs to counteract drive cable movement. Such torsion springs exhibit a torque rating that varies widely with angular displacement, and otherwise provides increasing resistance across its range of motion. This requires a robotic tool driver to alter the force required to move the drive cables during operation to account for continual changes in the torque resistance.

In some embodiments, the constant resistance provided by the first cable band 1012a may be altered and otherwise optimized by altering the thickness 1104 of the first cable band 1012a. The thicker the material (e.g., a metal) of the first cable band 1012a-d, the more torque resistance the first cable band 1012a is able to provide.

In other embodiments, the constant resistance provided by the first cable band 1012a may be altered by wrapping the first cable band 1012a around the first input shaft 1012a more tightly or more loosely. A tighter wrap will result in an increased constant torque force, and a looser wrap will result in a decreased constant torque force.

In yet other embodiments, the resistance provided by the first cable band 1012a may be altered or optimized by including one or more additional cable bands. Coupling a second cable band (not shown) to the first input shaft 1010a allows the constant torque resistance to be broken up into two load-bearing bands. In some applications, this may help provide a true (more even) constant force across the range of motion of the cable bands.

Accordingly, the first cable band 1012a may help maintain a minimum level of force on the first drive cable 808a, and prevent the first drive cable 808a from slackening. In contrast to conventional torsion springs that increase resistance with displacement, as the first input shaft 1010a is rotated, the torque resistance of the first cable band 1012a stays constant.

Figure 12A:
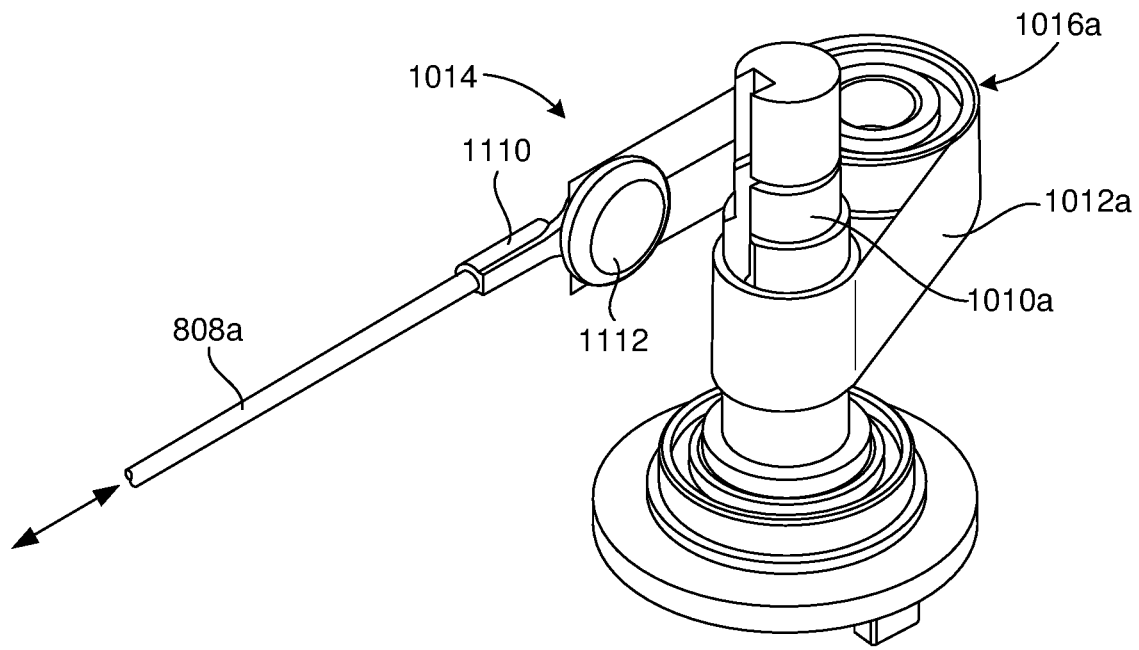
FIGS. 12A and 12B are opposing isometric side views of another embodiment of the first input shaft, the first cable band, and the first idler pulley cooperatively arranged for operation.
Figure 12B:
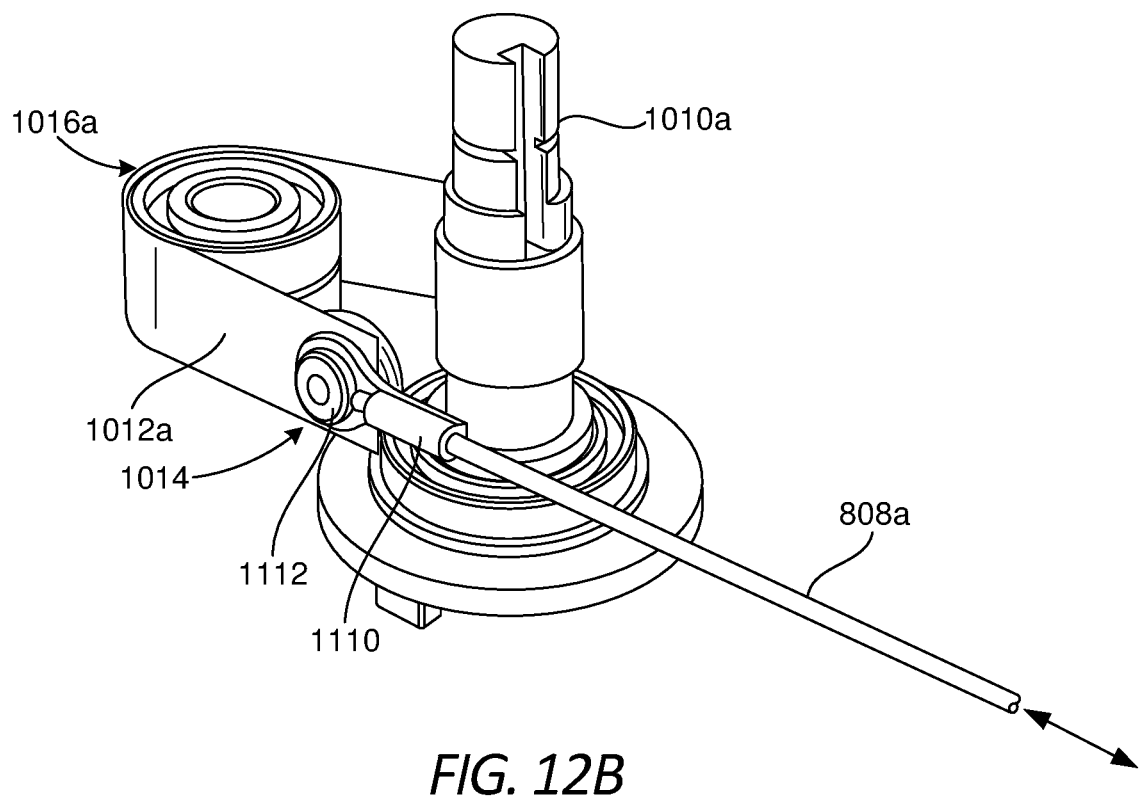

FIGS. 12A and 12B are opposing isometric side views of another embodiment of the first input shaft 1010a, the first cable band 1012a, and the first idler pulley 1016a cooperatively arranged for operation, according to one or more embodiments. More specifically, FIGS. 12A and 12B depict an alternative embodiment of the connector 1014 used to couple the first cable band 1012a to the first drive cable 808a. As with FIGS. 11A and 11B, while discussing specifics and details of the first input shaft 1010a, the first cable band 1012a, and the first idler pulley 1016a, the following description is equally applicable to any of the input shafts 1010a-d, cable bands 1012a-d, and idler pulleys 1016a-d described herein with reference to FIG. 10.

In the illustrated embodiment, the connector 1014 includes the fisheye connector 1110 secured to an end of the first drive cable 808a, and the mechanical fastener 1112 in the form of a rivet joint. To assemble the connector 1014 and thereby couple the first cable band 1012a to the first drive cable 808a, the mechanical fastener 1112 may be riveted through an aperture (occluded) defined by the fisheye connector 1110 and an aligned aperture (occluded) defined in the end of the first cable band 1012a.

Embodiments disclosed herein include:

A. A surgical tool that includes a drive housing having an input shaft arranged therein for rotation, an elongate shaft that extends from the drive housing, an end effector operatively coupled to a distal end of the elongate shaft, and a cable band coupled to the input shaft and operatively coupling the input shaft to a drive cable that extends to the end effector, wherein rotation of the input drive correspondingly moves the cable band and thereby controls longitudinal movement of the drive cable to articulate the end effector.

B. A method of operating a surgical tool that includes positioning the surgical tool adjacent a patient for operation, the surgical tool including a drive housing having an input shaft arranged therein for rotation, an elongate shaft that extends from the drive housing, an end effector operatively coupled to a distal end of the elongate shaft, and a cable band coupled to the input shaft and operatively coupling the input shaft to a drive cable that extends to the end effector. The method further including actuating a drive input coupled to the input shaft and thereby rotating the input shaft, and moving the cable band as the input drive rotates and thereby correspondingly controlling longitudinal movement of the drive cable to articulate the end effector.

Each of embodiments A and B may have one or more of the following additional elements in any combination: Element 1: wherein the cable band exhibits a height that is greater than a cross-sectional thickness of the cable band. Element 2: wherein the cable band comprises a constant force spring wrapped around the input shaft multiple times and provides a constant torque force that prevents the drive cable from slackening. Element 3: wherein the constant torque force remains constant across an entire range of motion of the cable band. Element 4: wherein the constant force spring comprises a ribbon or strip of a material. Element 5: wherein the cable band is routed at least partially around an idler pulley rotatably mounted within the drive housing. Element 6: wherein the idler pulley is arranged within the drive housing such that the cable band feeds the drive cable directly into the elongate shaft. Element 7: wherein the idler pulley includes an upper flange, a lower flange, and a trough that extends between the upper and lower flanges, and wherein the cable band is received within the trough and the upper and lower flanges help maintain the cable band within the trough. Element 8: wherein the cable band is directly coupled to the drive cable. Element 9: wherein the cable band is directly coupled to a hypotube that operatively couples the cable band to the drive cable. Element 10: further comprising a connector that couples the cable band to the drive cable. Element 11: wherein the connector comprises a fisheye connector secured to an end of the drive cable, a mechanical fastener extendable through an aperture defined by the fisheye connector, and a nut threadable to the mechanical fastener to secure the drive cable to the cable band. Element 12: wherein the connector comprises a fisheye connector secured to an end of the drive cable, and a rivet joint extendable through an aperture defined by the fisheye connector to secure the drive cable to the cable band.

Element 13: wherein the cable band comprises a constant force spring wrapped around the input shaft multiple times, the method further comprising providing a constant torque force from the constant force spring as the input shaft rotates and thereby preventing the drive cable from slackening. Element 14: further comprising adjusting the constant torque force by adjusting a thickness of the constant force spring. Element 15: further comprising adjusting the constant torque force by wrapping the cable band around the input shaft either more tightly or more loosely. Element 16: wherein the cable band is routed at least partially around an idler pulley rotatably mounted within the drive housing, the method further comprising positioning the idler pulley such that the cable band feeds the drive cable directly into the elongate shaft. Element 17: wherein the idler pulley includes an upper flange, a lower flange, and a trough that extends between the upper and lower flanges, the method further comprises receiving the cable band within the trough and helping maintain the cable band within the trough with the upper and lower flanges.

By way of non-limiting example, exemplary combinations applicable to A and B include: Element 2 with Element 3; Element 2 with Element 4; Element 5 with Element 6; Element 5 with Element 7; Element 10 with Element 11; Element 10 with Element 12; Element 13 with Element 14; Element 13 with Element 15; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
    a drive housing having an input shaft arranged therein for rotation;
    a shaft extending from the drive housing and having an end effector arranged at a distal end thereof;
    a drive cable extending within the shaft and operatively coupled to the end effector;
    a cable band comprising a constant force spring wrapped around the input shaft multiple times and operatively coupling the input shaft to the drive cable; and
    an idler pulley rotatably mounted within the drive housing, the cable band being routed at least partially around the idler pulley,
    wherein rotation of the input shaft moves the cable band and thereby controls longitudinal movement of the drive cable to articulate the end effector, and
    wherein the cable band provides a constant torque force that prevents the drive cable from slackening.

2. The surgical tool of claim 1, wherein the cable band exhibits a height that is greater than a cross-sectional thickness of the cable band.

3. The surgical tool of claim 1, wherein the constant torque force remains constant across an entire range of motion of the cable band.

4. The surgical tool of claim 1, wherein the constant force spring comprises a ribbon or strip of a material.

5. The surgical tool of claim 1, wherein the idler pulley is arranged within the drive housing such that the cable band feeds the drive cable directly into the shaft.

6. The surgical tool of claim 1, wherein the idler pulley includes an upper flange, a lower flange, and a trough extending between the upper and lower flanges, and wherein the cable band is received within the trough and the upper and lower flanges maintain the cable band within the trough.

7. The surgical tool of claim 1, wherein the cable band is directly coupled to the drive cable.

8. The surgical tool of claim 1, further comprising a connector that couples the cable band to the drive cable.

9. The surgical tool of claim 8, wherein the connector comprises:
    a fisheye connector secured to an end of the drive cable;
    a mechanical fastener extendable through an aperture defined by the fisheye connector; and
    a nut threadable to the mechanical fastener to secure the drive cable to the cable band.

10. The surgical tool of claim 8, wherein the connector comprises:
    a fisheye connector secured to an end of the drive cable; and
    a rivet joint extendable through an aperture defined by the fisheye connector to secure the drive cable to the cable band.

11. The surgical tool of claim 1, wherein the idler pulley is a free spinning structure.

12. A method of operating a surgical tool, comprising:
    positioning the surgical tool adjacent a patient for operation, the surgical tool including:
        a drive housing having an input shaft arranged therein for rotation;
        a shaft extending from the drive housing and having an end effector arranged at a distal end thereof;
        a drive cable extending within the shaft and operatively coupled to the end effector;
        a cable band coupled to the input shaft and operatively coupling the input shaft to the drive cable; and
        an idler pulley rotatably mounted within the drive housing, the cable band being routed at least partially around the idler pulley actuating a drive input coupled to the input shaft and thereby rotating the input shaft;
    moving the cable band as the input shaft rotates and thereby correspondingly controlling longitudinal movement of the drive cable to articulate the end effector; and
    removing slack in the drive cable with a constant torque force provided by the cable band.

13. The method of claim 12, wherein the cable band comprises a constant force spring wrapped around the input shaft multiple times.

14. The method of claim 13, further comprising adjusting the constant torque force by adjusting a thickness of the constant force spring.

15. The method of claim 13, further comprising adjusting the constant torque force by wrapping the cable band around the input shaft either more tightly or more loosely.

16. The method of claim 12, further comprising positioning the idler pulley such that the cable band feeds the drive cable directly into the shaft.

17. The method of claim 16, wherein the idler pulley includes an upper flange, a lower flange, and a trough that extends between the upper and lower flanges, the method further comprises receiving the cable band within the trough and helping maintain the cable band within the trough with the upper and lower flanges.

18. A surgical tool, comprising:
    a drive housing having an input shaft arranged therein for rotation;
    a shaft extending from the drive housing and having an end effector arranged at a distal end thereof;
    a drive cable extending within the shaft and operatively coupled to the end effector;

a cable band coupled to the input shaft at a first end and directly coupled to the drive cable at a second end; and an idler pulley rotatably mounted within the drive housing, the cable band being routed at least partially around the idler pulley, wherein rotation of the input shaft moves the cable band and thereby controls longitudinal movement of the drive cable to articulate the end effector.

19. The surgical tool of claim 18, wherein the cable band comprises a constant force spring wrapped around the input shaft multiple times and provides a constant torque force that prevents the drive cable from slackening.

20. The surgical tool of claim 18, wherein the idler pulley is arranged within the drive housing such that the cable band feeds the drive cable directly into the shaft.

* * * * *